(12) United States Patent
Flore (10) Patent No.: US 6,323,183 B1
(45) Date of Patent: Nov. 27, 2001

(54) COMPOSITION FOR AND METHOD OF TREATMENT USING TRITERPENOIDS

(76) Inventor: Ornella Flore, 430 E. 63$^{rd}$ Apt. 3K, New York, NY (US) 10021

( * ) Notice: Subject to any disclaimer, the term of this patent is extended or adjusted under 35 U.S.C. 154(b) by 0 days.

(21) Appl. No.: 09/324,473

(22) Filed: Jun. 2, 1999

(51) Int. Cl.$^7$ .................................................... A61K 31/70
(52) U.S. Cl. .................................. 514/26; 435/FOR 161; 935/36
(58) Field of Search ........................ 514/25, 26; 536/4.1, 536/5; 935/36; 435/FOR 161

(56) References Cited

U.S. PATENT DOCUMENTS

| | | | |
|---|---|---|---|
| 5,128,150 | * | 7/1992 | Shanbrom .............................. 424/533 |
| 5,527,890 | * | 6/1996 | Rao et al. ................................. 536/5 |
| 5,679,644 | * | 10/1997 | Rao et al. ............................... 514/26 |
| 5,763,582 | * | 6/1998 | Rao et al. ................................. 536/5 |
| 5,837,690 | * | 11/1998 | Rao et al. ............................... 514/26 |

OTHER PUBLICATIONS

Saponns. edited by Hostettman, K. and A. Marston, publ. by Cambridge University Press, pp. 247–250 and 274–275, 1995.*

Naturally Occurring Glycosides. edited by Raphael Ikan, publ. by John Wiley & Sons, pp. 295–309 (Chapter 9—Saponins), 1999.*

Shvarev et al. "Effect of triterpenoid compounds from Glycyrrhiza glabra on experimental tumors", Vop. Izuch. Ispol'z. Solodki SSSR, Akad. Nauk SSSR, p. 167–170, 1966.*

* cited by examiner

Primary Examiner—Howard C. Lee
(74) Attorney, Agent, or Firm—Thomas A. O'Rourke; Wyatt, Gerber & O'Rourke (57) ABSTRACT

Methods and compositions for treating Kaposi's sarcoma and Epstein Barr virus using a a therapeutic derivative of a triterpenoid acid and derivatives thereof are disclosed.

18 Claims, 10 Drawing Sheets

| No cells surviving Days of treatment | BJAB Control | alcohol 0.5% | alcohol 1% | Ac. Glyc. 2mM | Ac.Glyc. 4mM |
|---|---|---|---|---|---|
| 0 | 4.00E+05 | 4.00E+05 | 4.00E+05 | 4.00E+05 | 4.00E+05 |
| 2 | 1.50E+06 | 1.00E+06 | 6.00E+05 | 1.00E+06 | 8.00E+05 |
| 4 | 5.40E+06 | 4.90E+06 | 1.60E+06 | 2.40E+06 | 1.60E+06 |
| 6 | 6.00E+06 | 5.00E+06 | 3.00E+06 | 4.00E+06 | 2.30E+06 |

Figure 1

| Days of Treatment | BC-3 | Alcohol 0.5% | Alcohol 1% | Glyc. Ac. 2mM | Glyc. Ac. 4mM |
|---|---|---|---|---|---|
| 0 | 4.00E+05 | 4.00E+05 | 4.00E+05 | 4.00E+05 | 4.00E+05 |
| 2 | 1.00E+06 | 8.00E+05 | 6.00E+05 | 3.00E+05 | 6.00E+04 |
| 4 | 2.50E+06 | 2.50E+06 | 1.70E+06 | 7.00E+05 | 8.00E+03 |
| 6 | 3.00E+06 | 3.00E+06 | 2.50E+06 | 1.00E+06 | 10 |

| Days of Treatment | BC-1 | Alcohol 1% | Glyc. Ac. 2mM | Glyc. Ac. 4mM | Glyc. Ac. 3mM |
|---|---|---|---|---|---|
| 0 | 4.00E+05 | 4.00E+05 | 4.00E+05 | 4.00E+05 | 4.00E+05 |
| 2 | 8.70E+05 | 6.00E+05 | 6.00E+05 | 5.50E+05 | 6.20E+05 |
| 4 | 2.20E+06 | 1.10E+06 | 7.10E+05 | 3.50E+05 | 5.90E+05 |
| 6 | 3.00E+06 | 2.00E+06 | 1.10E+06 | 3.50E+05 | 7.60E+05 |

FIGURE 4

| days of treatment | BC-2 | Alcohol 1% | Glyc. Ac. 2mM | Glyc. Ac. 4mM |
|---|---|---|---|---|
| 0 | 4.00E+05 | 4.00E+05 | 4.00E+05 | 4.00E+05 |
| 2 | 9.40E+05 | 7.60E+05 | 6.70E+05 | 6.00E+05 |
| 4 | 2.20E+06 | 1.90E+06 | 1.00E+06 | 6.00E+05 |
| 6 | 3.50E+06 | 3.40E+06 | 9.00E+05 | 6.50E+05 |

COMPOSITION FOR AND METHOD OF TREATMENT USING TRITERPENOIDS

BACKGROUND OF THE INVENTION

Acquired Immunodeficiency Syndrome (AIDS) is one of the most significant infections to appear in recent history. This epidemic is not confined to a single segment of the population nor is its spread blocked by natural barriers or international boundaries. Millions have died in Africa and many more individuals are infected worldwide. In the United States more than 100,000 people have died and at least 1 million more are presently infected with the virus. Although there are some new drug treatments that are currently available for treating the disease, this pandemic shows no signs of abating.

AIDS is a disease of an acquired immunodeficiency syndrome in humans caused by HIV. The first description of the disease was in 1981. Its causative agent, HIV, was discovered in 1983. As of 1993 it is estimated that about 13 million people were infected with HIV worldwide and this number has increased to about 21 million in 1996. See B. Jasny, Science, 260(5112), 1219 (1993) and P. Piot, Science, 272(5270), 1855 (1996).

AIDS was first diagnosed in male homosexuals who exhibited a variety of infections of fungal (*Candida albicans*), protozoal (*Pneumocystis carinii*), and viral (*Herpes zoster*) origin. Many of these individuals also had an increased incidence of kaposi sarcoma and lymphoma. They had a depressed T helper/T suppressor lymphocyte cell ratio and an absence of delayed hypersensitivity responses. Collectively, these observations suggested a deficiency in cell-mediated immunity.

The causative agent in AIDS is an RNA retrovirus called the human immunodeficiency virus (HIV-1 or HIV-2). HIV possesses an envelope glycoprotein (gp120) that has a high affinity for the $CD_4$ receptor on T helper cells and other target cells. These other target cells include bone marrow stem cells, macrophages, endothelial cells, glial cells, lymph node, dendritic cells, bowel enterochromaffm cells, cervical eptithlium and possibly Langerhans cells. However, it is the effects of HIV on T-helper cells that are the best known. The infectious process begins when the virus penetrates the body and enters the blood stream. Binding of HIV to $CD_4$ target cells involves interaction of the external envelope glycoprotein molecule gp120 with the $CD_4$ molecule, although other cell receptors may be involved. The virus next enters the target cell, or is internalized, through fusion of the viral envelope with the target cell membrane. Through this fusion, the virus loses its coat, and releases its RNA core and reverse transcriptase enzyme into the host cell cytoplasm.

The HIV reverse transcriptase enzyme copies the RNA message producing first a single-stranded, and then a double-stranded, DNA (circular complementary DNA). This newly formed double-stranded DNA becomes incorporated into the host chromosomal DNA once it enters the host cell nucleus. This incorporated viral DNA may remain dormant or, upon activation, will produce viral messenger RNA (mRNA). The viral MRNA codes for proteins that are important in viral replication. Glycoprotein will then envelop the RNA genome resulting in the production of infectious viral particles; completed viral particles are then released to infect other cells.

In the efforts to combat the disease several drugs have been approved by the FDA for treating this disease, including azidovudine (AZT), didanosine (dideoxyinosine, ddI), d4T, zalcitabine (dideoxycytosine, ddC), nevirapine, lamivudine (epivir, 3TC), saquinavir (Invirase), ritonavir (Norvir), indinavir (Crixivan), and delavirdine (Rescriptor). See M. I. Johnston & D. F. Hoth, Science, 260(5112), 1286–1293 (1993) and D. D. Richman, Science, 272(5270), 1886–1888 (1996).

Many of the drugs currently approved for AIDS treatment utilize inhibition of viral proliferation and are viral reverse transcriptase inhibitors or viral protease inhibitors. Other protease inhibitors, such as nelfinavir and improved saquinavir, are either in development or close to approval. An AIDS vaccine (Salk's vaccine) has been tested and several proteins which are chemokines from CD8 have been discovered to act as HIV suppressors.

In addition to the synthetic nucleoside analogs, proteins, and antibodies noted above, several plants and substances derived from plants have been found to have in vitro anti-HIV activity, such as *Lonicera japonica* and *Prunella vulgaris*, and glycyrrhizin from *Glycyrrhiza radix*. See R. S. Chang & H. W. Yeung, Antiviral Research, 9, 163–175 (1988) and M. Ito, et al., Antiviral Research, 7, 127–137 (1987).

Despite all of the available pharmaceuticals for the treatment of HIV, there is still no cure for the deadly disease. HIV viruses continue to mutate and become resistant to existing drugs such as the reverse transcriptase inhibitors and protease inhibitors. Recently, a therapy of using two (2) or three (3) anti-HIV drugs in combination has been found effective in significantly lowering the HIV loads in AIDS patients. The results have been promising, however the virus continues to develop resistance to the drugs and the long-term outcome (survival and cure rates) is still unknown. Thus, the medical communities throughout the world continue to search for drugs that can prevent HIV infections, treat HIV carriers to prevent them from progressing to full-blown deadly AIDS, and treat the AIDS patient.

As noted above, many AIDS suffers are also afflicted with Kaposi's sarcoma. In fact, Kaposi's sarcoma is the most common neoplasm occurring in persons with acquired immunodeficiency syndrome (AIDS). Approximately 15–20% of AIDS patients develop this neoplasm which rarely occurs in non-AIDS infected individuals. Epidemiologic evidence suggests that AIDS-associated Kaposi's sarcoma(AIDS-KS) may have an infectious etiology. Kaposi's sarcoma-associated herpesvirus (KSHV/HHV8) is a new human herpesvirus found in all KS lesions and considered the infectious agent. Gay and bisexual AIDS patients are approximately twenty times more likely than hemophiliac AIDS patients to develop Kaposi's sarcoma, and Kaposi's sarcoma may be associated with specific sexual practices among gay men with AIDS. Kaposi's sarcoma is uncommon among adult AIDS patients infected through heterosexual or parenteral HIV transmission, or among pediatric AIDS parenteral HIV transmission, or among pediatric AIDS patients infected through vertical HIV transmission. Agents previously suspected of causing Kaposi's sarcoma include cytomegalovirus, hepatitis B virus, human papillomavirus, Epstein-Barr virus, human herpesvirus 6, human immunodeficiency virus (HIV), and Mycoplasma penetrans. Non-infectious environmental agents, such as nitrite inhalants, also have been proposed to play a role in Kaposi's sarcoma tumorigenesis. Extensive investigations, however, have not demonstrated an etiologic association between any of these agents and AIDS-KS.

Herpesviruses, such as Kaposi's sarcoma-associated herpesvirus (KSHV), are a family of large double stranded DNA-containing viruses many members of which are important human pathogens. A ubiquitous property of the herpesviruses is their capacity to cause both acute lytic (productive) and latent infections in the human host, each of which is characterized by marked differences in viral transcription, DNA replication and in DNA structure.

Kaposi's sarcoma-associated herpesvirus (KSHV), or human herpesvirus 8 (HHV 8), has been detected in all four clinical forms of Kaposi's sarcoma: AIDS related (epidemic), European (sporadic), Transplant-associated (iatrogenic) and African (endemic). While this virus is generally absent from normal control tissues, it is present in the vast majority of AIDS- as well as non-AIDS-related KS lesions, suggesting that it is not simply an opportunistic infection in HIV-infected patients. See Chang Yet al, Identification of herpesvirus-like DNA sequences in AIDS-associated Kaposi's sarcoma. Science 266:1865–1869, 1994, Moore P S, Chang Y: Detection of herpesvirus-like DNA sequences in Kaposi's sarcoma lesions from persons with and without HIV infection. N Engl J Med 332:1181–1185, 1995, Dupin N, et al, Herpesvirus-like DNA sequences in patients with Mediterranean Kaposi's sarcoma. Lancet 345:761–762, 1995.

Furthermore, KSHV is consistently present in a specific type of non-Hodgkin's lymphoma (NHL), frequently, not exclusively, occurring in patients with AIDS, namely the primary effusion lymphomas (PELs), also called body cavity-based lymphomas (BCBLs). See Cesarman E, et al, Kaposi's Sarcoma-associated Herpesvirus-like DNA sequences in AIDS-related body cavity-based lymphomas. N Eng J Med 332:1186–1191, 1995, Nador R G, et al, Herpes-like DNA sequences in a body-cavity-based lymphoma in an HIV-negative patient (Letter to the Editor). N Engl J Med 333:943, 1995.

KSHV is also present in a significant proportion of cases of multicentric Castleman's disease, a poorly understood disorder characterized by generalized lymphadenopathies and immune disregulation. See Soulier J, et al Kaposi's sarcoma-associated herpesvirus-like DNA sequences in multicentric Castleman's disease. Blood 86:1275–1280, 1995. Recently, the presence of KSHV in bone marrow dendritic cells of all patients with multiple myeloma has been reported. See Rettig M B, et al Kaposi's sarcoma-associated herpesvirus infection of bone marrow dendritic cells from multiple myeloma patients. Science 276:1851–1854, 1997. While this last finding remains controversial, it raises the possibility of involvement of KSHV in a very frequent type of cancer affecting non-immunosuppressed individuals.

KSHV, as all other herpesvirus, has a litic and a latent cycle. Only a few antiviral agents have been used for activity against KSHV. Several studies determined the effect of acyclovir, gancyclovir, foscarnet and cidofovir in their ability to prevent lytic replication of KSHV in response to phorbol ester (TPA) induction. See Kedes D H, D. G: Sensitivity of Kaposi's sarcoma-associated herpesvirus replication to antiviral drugs. J Clin Invest 99:2082–2086, 1997, Medveczky M M, et al In vitro antiviral drug sensitivity of the Kaposi's sarcoma-associated herpesvirus. Aids 11:1327–1332, 1997, Costagliola D, et al Can anitviral agents decrease the occurrence of Kaposi's sarcoma? Clinical Epidemiology Group from Centres d'Information et de SOins de l'Immunodeficience Humaine (letter). Lancet 346:578, 1995, and Flore O, et al, Effect of DNA synthesis inhibitors on Kaposi's sarcoma-associated herpesvirus cyclin and major capsid protein gene expression. AIDS Res Hum Retroviruses vol. 13, 14: 1229–1233, 1997.

These drugs target only the litic viral replication, the latent viral infection cannot be controlled. Long-term treatment with these agents may be beneficial after the malignancy has developed, but is not resolutive. Once the treatment is interrupted the clinical reactivation can recur since the virus cannot be completely eliminated as the viral latent cycle is not affected. Accordingly, there still remains a need for a drug which inhibits the latent cycle of KSHV/HHV8 and is free from deleterious side effects.

SUMMARY OF THE INVENTION

The present invention relates to the use of a triterpenoid preferably a Glycyrrhizic acid (Glycyrrhizin) to inhibit the transcription of viral latent genes and the consequential viral latent cycle at doses that do not affect the uninfected cells. Using Glycyrrhizic acid and derivatives, the KSHV infected cells are completely killed six days after treatment.

BRIEF DESCRIPTION

DETAILED DESCRIPTION

Figure 4:
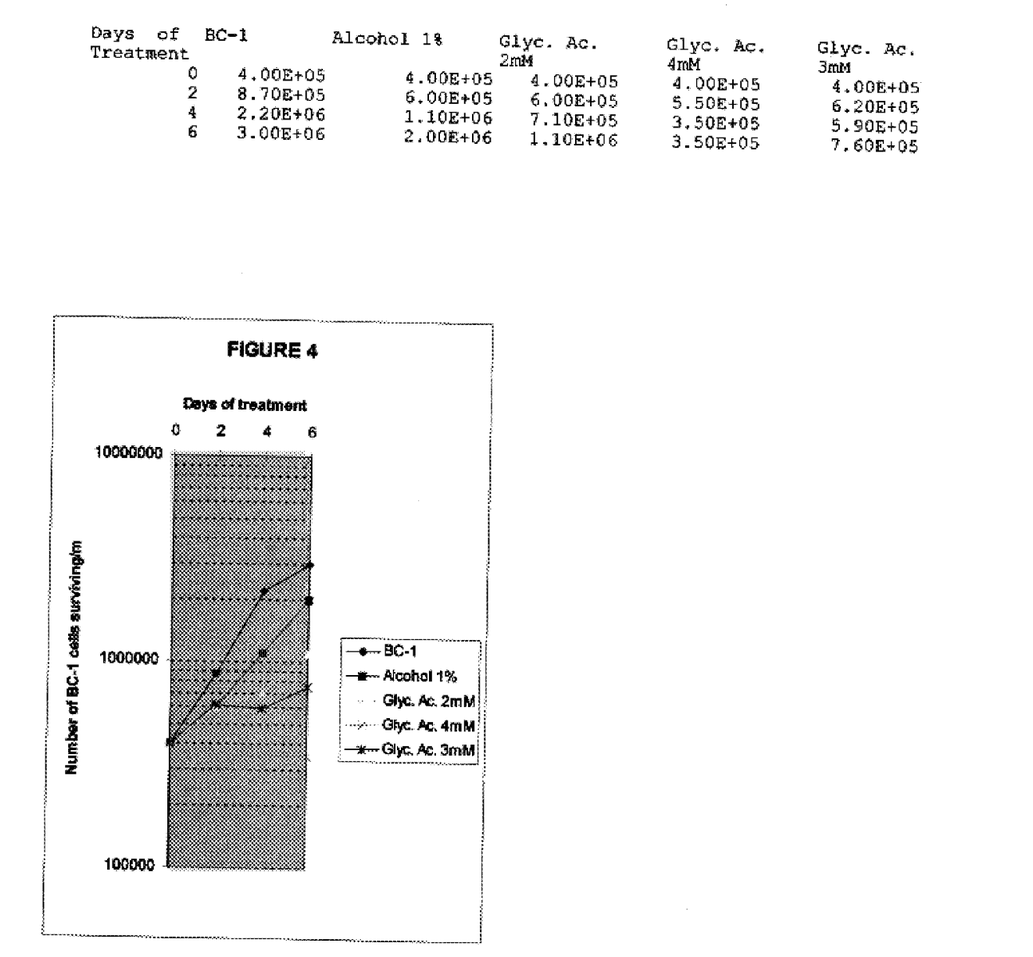
FIG. 4 demonstrates the effect of glycyrrhizic acid on BC-1 cells growth curve.
Figure 7:
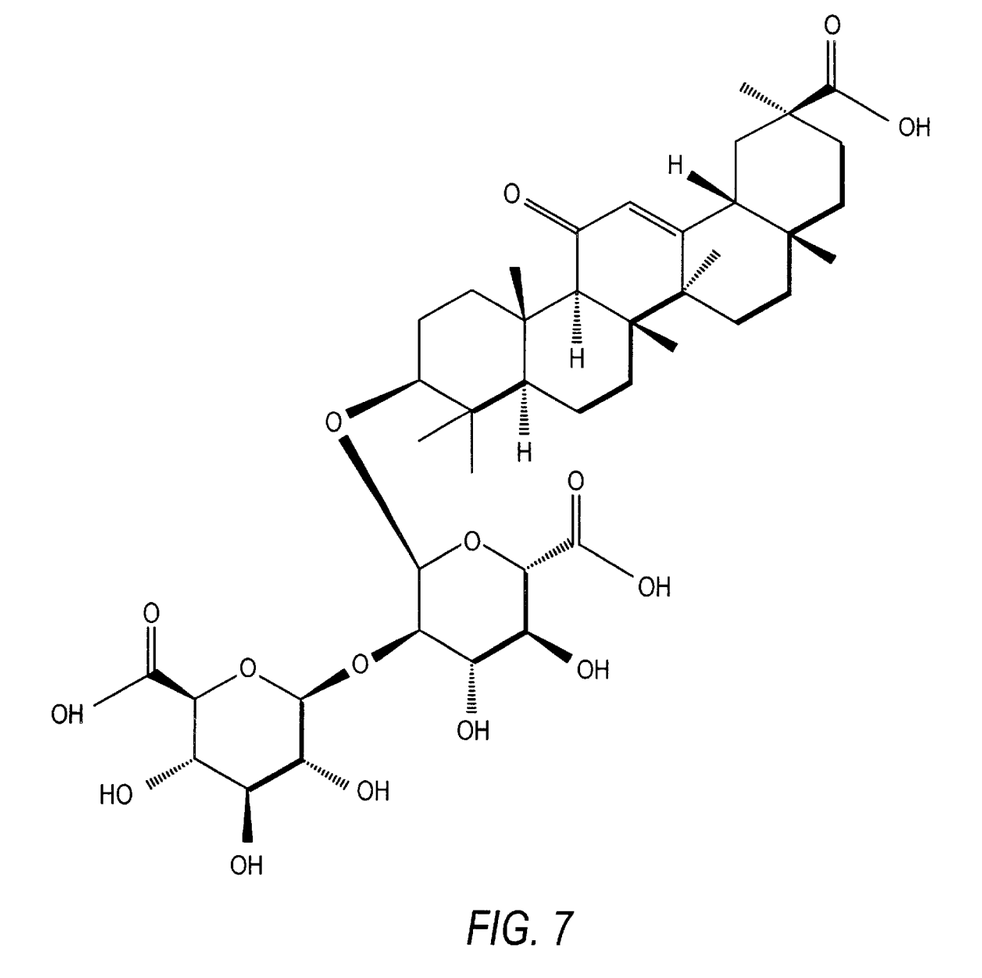
FIG. 7 shows the structural formula of glycyrrhizic acid.
Figure 8:
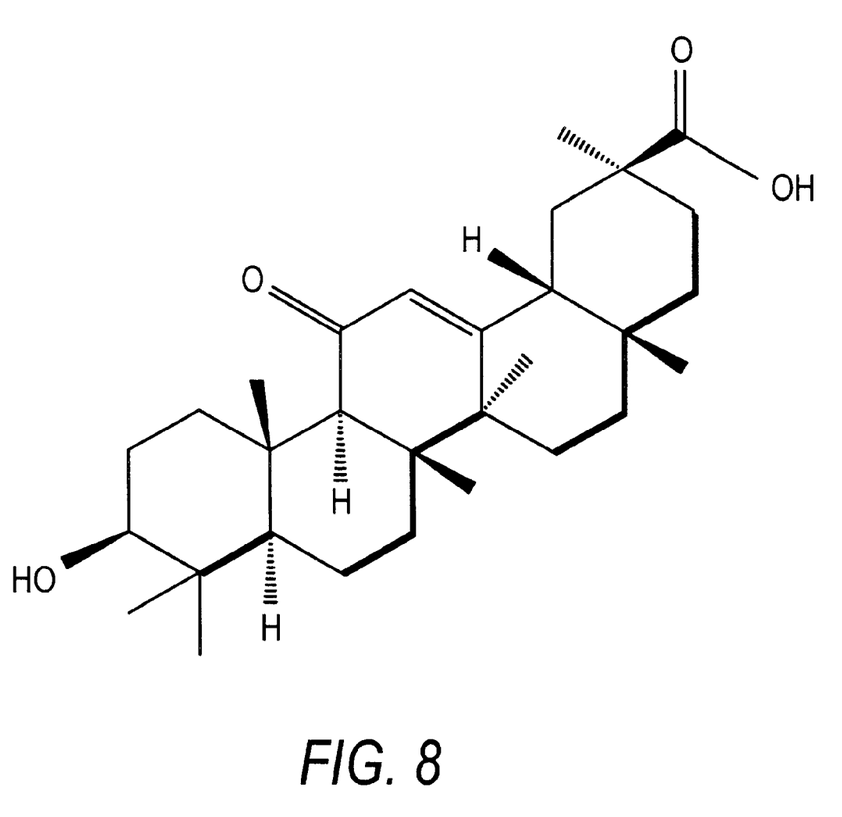
FIG. 8 shows the structural formula of glycyrrhetinic acid which when combined with two molecules of glucuronic acid forms glycyrrhizic acid.
Figure 9:
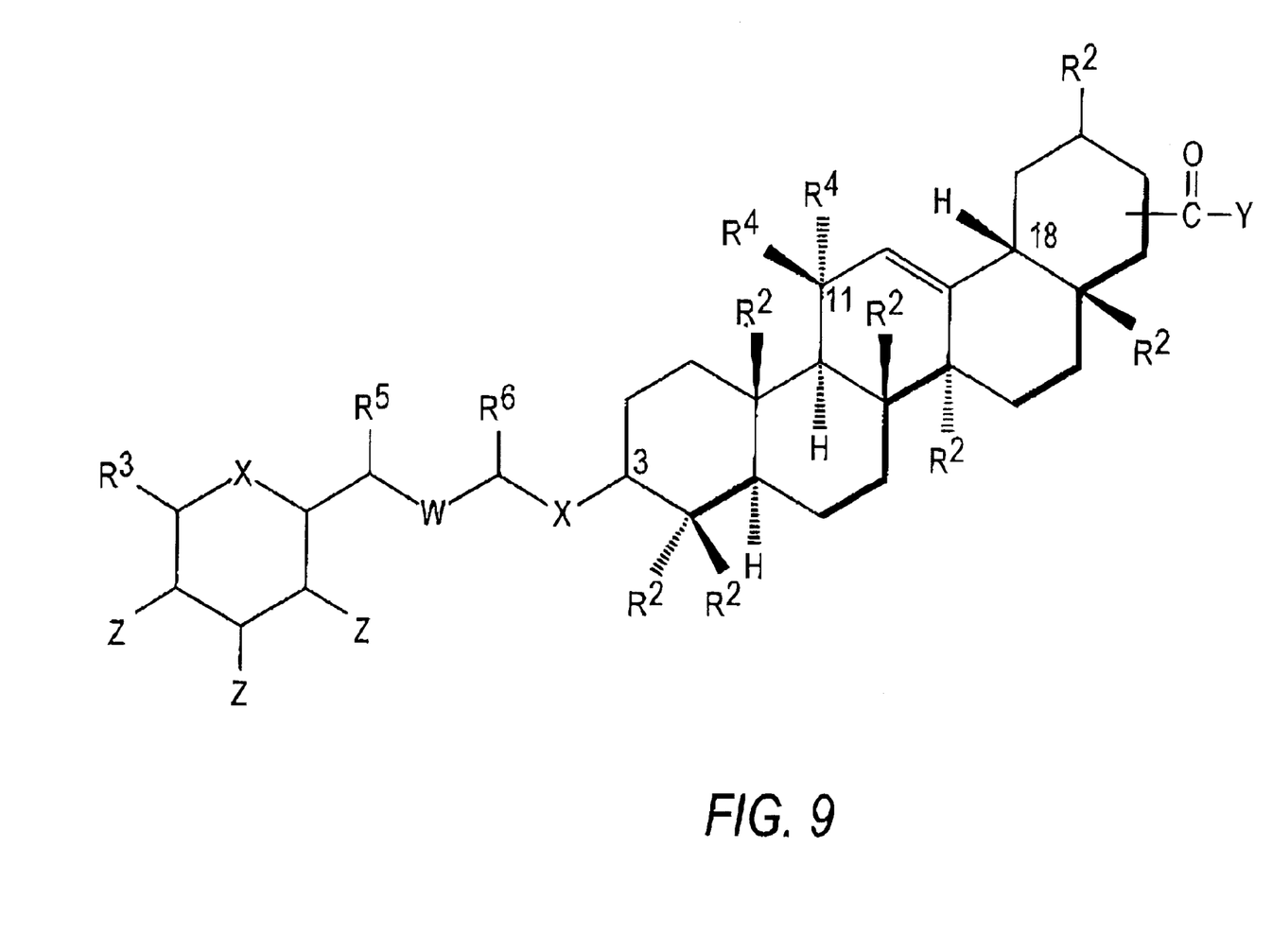
FIG. 9 shows a further example of a triterpenoid acid derivatives of the present invention.

The present invention is directed to triterpenoid acid derivatives that exhibit pharmacophobic activities for the treatment of Kaposi's sarcoma (KSHV) preferably glycyrrhizic acid and its salts. Examples of triterpenoids of the type useful in the present invention include those disclosed in U.S. Pat. No. 5,837,690 the disclosure of which are incorporated herein by reference. FIG. 4 shows the structural formula for the triterpenoid acid of the present invention and FIG. 7 shows a further example of a triterpenoid acid derivative of the present invention wherein:

$Y=OR^1$, $NR^1_2$, $O-M^1$;

$R^1=H$, LOWER ALKYL, $M^1=Na.^+$, $K^+$, $Mg^{++}$, $Ca^{++}$ ions;

$R^2=CH_2OR_1$ or $CH_3$;

$R^3=H$, $CH_3$, lower alkyl, COY, $CH_2OH$, $CH_2OCH_2CH=CH_2$, $CH_2OSO-_3M^1$;

$Z=NR^1$, $NR.^1Ac$, $NR^1Bz$, H, $OCH_3$, lower alkyl, OH, $SO_3-M^1$, $OCH_2CH=CH_2$, $OCH_2CO_2H$ or O-glucoside wherein a glucoside includes glucose, fucose, galactose, mannose, arabinose or xylose;

$R^4=H$, OH, $SO_3-M^1$, $NH(CH_2)_nNH^2$, or $NH-Ph-(NH_2)_n$ wherein n=1–8 and Ph is a phenyl or naphthyl ring substituted with up to 3 amine functionalities and the remaining substitutions can be H, $R^1$, $R^2$ or $CO_2R^1$;
or both $R^4$ taken together are oxo;
$R^5$ and $R^6$=H, $R^1$ or taken together to form a 5 or 6 membered carbocyclic ring;
X=O, S, $NR^1_2$
W=C=O, C=$CR^1_2$, $CR^1CR^1_3$, $CR^1$—$CR^1_2OR^1$, $COR^1$—$CR^1OR^1_2$, $COR^1CR^1_2OR^1$, $CR^1CR^1_2NR^1_2$, $CR^1CR^1_2OCR^1COY$;

Glycyrrhizin, as used herein to denote glycyrrhizinic acid or a salt thereof, is a well-known substance as effective ingredient of Licorice used heretofore as medicine or sweetener. At present, isolated and refined glycyrrhizin is used widely in many fields of application and, especially, free acids, as well as sodium, potassium and ammonium salts including acidic salts of glycyrrhizin are used most widely or studied for their properties, all of these substances exhibiting marked sweetness and various pharmaceutical activities.

Glycyrrhizic acid (Glycyrrhizin) (FIG. 5) consists of one molecule of glycyrrhetinic acid (FIG. 6) and two molecules of glucuronic acid. Glycyrrhizic acid is freely soluble in hot water and alcohol. Ammonium glycyrrhizinate pentahydrate is soluble in ammonia water, ethanol, glacial acetic acid. Glycyrrhizic acid (Glycyrrhizin) derivatives for Na+, K+ and triterpenoids compounds, which would work on viral inhibition, can be dissolved in chloroform, dioxane, alcohol, pyridine, acetic acid and most organic solvents. The active part of the compound is believed to be the triterpenoid part (FIG. 4) (without the glucuronic acid) which is similar to steroids. Indeed this portion has an antinflammatory and antiulcerative activity. All derivatives without the glucuronic part have an antinflammatory activity. The two molecules of glucuronic acid make the compound more hydrosoluble and rich in negative charges, it becomes less toxic but also less active if it's used at the same concentration.

The compositions of the present invention can be administered to a patient by intravenous or parenteral injection, topical application, etc., in an amount to prevent or treat the Kaposi's sarcoma (KSHV). The triterpenoid acid derivatives compounds of the invention can be administered to a subject in need thereof to treat the subject by either prophylactically preventing disease or relieving it after it has begun. The invention compounds are preferably administered with a pharmaceutically acceptable carrier, the nature of the carrier dependant on the chemical properties of the compounds, including solubility properties, and/or the mode of administration. For example, if oral administration is desired, a solid carrier may be selected, and for I.V. administration a liquid salt solution carrier may be used.

The formulation of choice can be accomplished using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the invention compounds directly in transdermal formulations with permeation enhancers such as DMSO. Other topical formulations can be administered to treat certain disease indications.

Typically, the compounds of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on the responsiveness of the patient. Other effective dosages can be readily determined by one of ordinary skill in the art through routine trials establishing dose response curves.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

The compounds of the instant invention may also be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles. The compounds of the present invention can be mixed with compatible, pharmaceutically acceptable excipients.

Certain methods of preparing dosage forms of the invention compounds are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated. The various compounds of the present invention can be used by themselves or in combination with pharmaceutically acceptable excipient materials as described above.

In a preferred embodiment the glycyrrhizic acid or derivative can be administered orally, parenterally or through intravenous injections. The preferred dose range is 2.5 mg to 50 mg/kg. A preferred injection medium is water containing suitable stabilizers, solubilizers and/or buffers. For topical treatment suitable dosage forms are creams, ointments and medicated plasters. Glycyrrhizic salt preparations can be dissolved in water or phosphate buffer and neutralized with NaOh.

Materials and Methods

The Glycyrrhizic acid (as ammonium salt supplied by Sigma) is dissolved in 25% of ethanol at 100 mM and adjusted to pH 6.8 with 1 N sodium hydroxide. The maximum inhibition activity with no effect on cell cycle is achieved with 4 mM, the dose-dependent range is within 2 mM to 5 mM.

Cell Culture Used for the Tests

BC-3 is a cell line established from a HIV negative patient with a primary effusion lymphoma. See Arvanitakis L, et al Establishment and characterization of a primary effusion (body cavity-based) lymphoma cell line (BC-3) harboring Kaposi's sarcoma-associated herpesvirus (KSHV/HHV-8) in the absence of Epstein-Barr virus. Blood 88:2648–2654, 1996. The cells are latently KSHV-infected, but lacks EBV, and can be induced to enter lytic replication and viral production by treatment with TPA or with butyrate. BC-3 has an intact KSHV genome and is suitable for the isolation and study of KSHV.

BJA-B is an Epstein-Barr virus (EBV)-negative lymphoblastoid cell line established from an African Burkitt's lymphoma, KSHV negative cell line. See Menezes J, et al, Establishment and characterization of an Epstein-Barr virus (EBV)-negative lymphoblastoid B cell line (BJA-B) from an exceptional, EBV-genome-negative African Burkitt's lymphoma. Biomedicine July 1975; 22(4): 276–84. These cells are used as controls. Cells are cultured at concentration of 4×10$^5$/ml in RPMI with 20% of fetal calf serum in the presence or absence of different drug concentrations.

BC-1 and BC-2 are cell lines established from two different HIV positive patients with non-Hodgkins lymphoma, specifically body cavity-based lymphomas. The cells are KSHV/EBV-infected and can be induced to enter lytic replication and viral production by treatment with TPA or with butyrate. These cells have an intact KSHV and EBV genomes and are ideal for KSHV and EBV isolation and study.(Cesarman, E. et al., Blood October 1995; 86(7): 2708–14.

RNA Extraction and Northern Blot Analysis to Measure the Transcription of Viral Genes Total RNA was extracted using RNAzol B (Tel-Test Inc., Friendswood, Tex.) according to the manufacturer's instructions, and Poly A+ RNA was selected with Poly A+ Tract kit (Promega, Madison, Wis.). To eliminate any contaminating DNA, the RNA samples were treated with 2 U RNAse free DNAse (Promega).

For Northern blot analysis, 1 μg/ml of each mRNA sample was electrophoresed in 1.5% formaldehyde agarose gel and then transferred to a Gene Screen nylon membrane (Du Pont, Boston, Mass.) overnight with 20× SSC. Filters were UV-cross-linked to fix the RNA and hybridized at 42° C. with probes obtained by PCR amplification of KSHV cyclin, v-FLIP and LANA (orf 73) genes (20) and labeled by $^{32}$P random priming (Amersham Life Science, Buckinghamshire, England). Human β-actin probe was used as a quantitative control to measure the total mRNA. Membranes were washed twice at room temperature and twice at 65° C. then exposed.

Results

Figure 1:
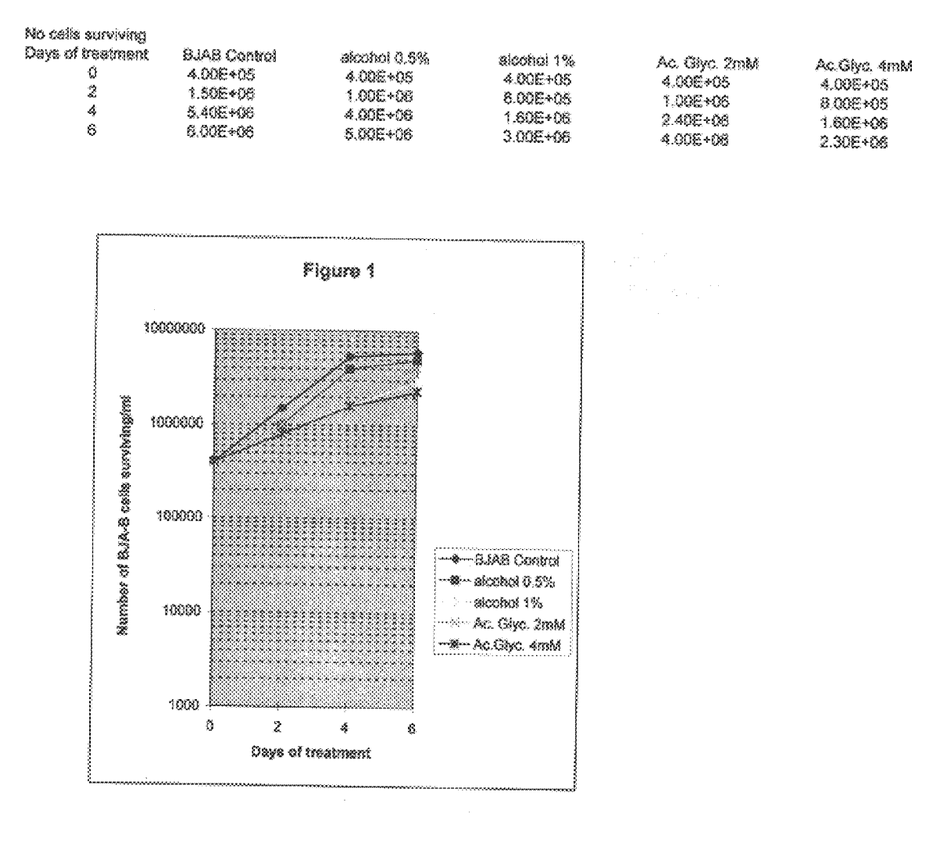
FIG. 1 shows the effect of Glycyrrhizic acid on BJAB cells growth curve.

FIG. 1 shows the effect of Glycyrrhizic acid on BJAB cells growth curve. Cells are treated for six days with alcohol 0.5% and 1%, Glycyrrhizic acid 2 mM and 4 mM in alcohol 0.5% and 1% respectively. Glycyrrhizic acid has no effect on the cells proliferation.

Figure 2:
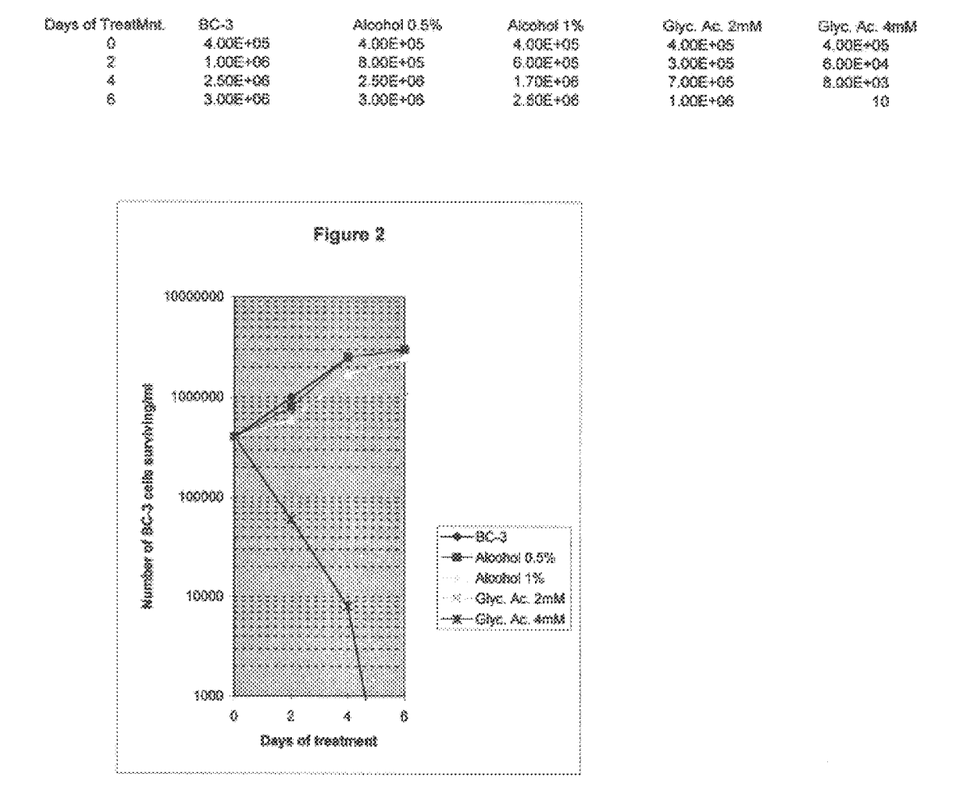
FIG. 2 shows the effect of Glycyrrhizic acid on BC-3 cells growth curve.

FIG. 2 shows the effect of Glycyrrhizic acid on BC-3 cells growth curve. The cells are treated for six days with alcohol 0.5% and 1%, Glycyrrhizic acid 2 mM and 4 mM in alcohol 0.5% and 1% respectively. Cells growth is 50% inhibited by Glycyrrhizic acid 2 mM, while treatment with Glycyrrhizic acid 4 mM determines cell death.

Figure 3:
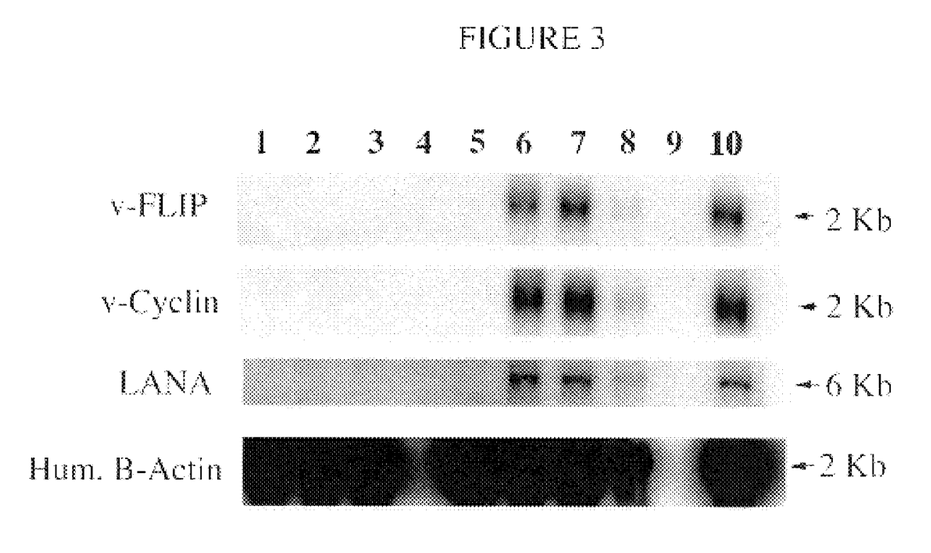
FIG. 3 shows Northern Blot of mRNA extracted from BJA-B and BC-3 cells after six days treatment.

FIG. 3 shows Northern Blot of mRNA extracted from BJA-B and BC-3 cells after six days treatment.
Lane: 1 BJA-B
Lane: 2 BJA-B treated with Glycyrrhizic acid 2 mM
Lane: 3 BJA-B treated with Glycyrrhizic acid 4 mM
Lane: 4-
Lane: 5 BJA-B treated with alcohol 1%
Lane: 6 BC-3
Lane: 7 BC-3 treated with Glycyrrhizic acid 2 mM
Lane: 8 BC-3 treated with Glycyrrhizic acid 4 mM
Lane: 9-
Lane: 10 BC-3 treated with alcohol 1%

On the left side are indicated the probes used. On the right side are indicated the size of the transcripts. All probes correspond to viral latent genes, except the human b actin which is used as a quantitative control to measure the transcription of total cellular mRNA.

Lanes 1–5 are the BJA-B cells which are not infected by KSHV, therefore they are negative, except for the b actin, which shows that the transcription of total cellular mRNA is not inhibited by the treatment with Glycyrrhizic acid.

Lane 6 is the positive control. Glycyrrhizic acid 2 mM does not show any effect on the viral latent genes transcription (lane 7), while at 4 mM the transcription is almost totally inhibited (lane 8). Treatment with alcohol 1%, which is the percentage present in the Glycyrrhizic acid 4 mM, does not affect the transcript products. This result excludes the possibility that the inhibition is due to alcohol toxicity. Equal presence of β actin in all samples confirms that the compound does not have any effect on cellular mRNA.

Figure 5:
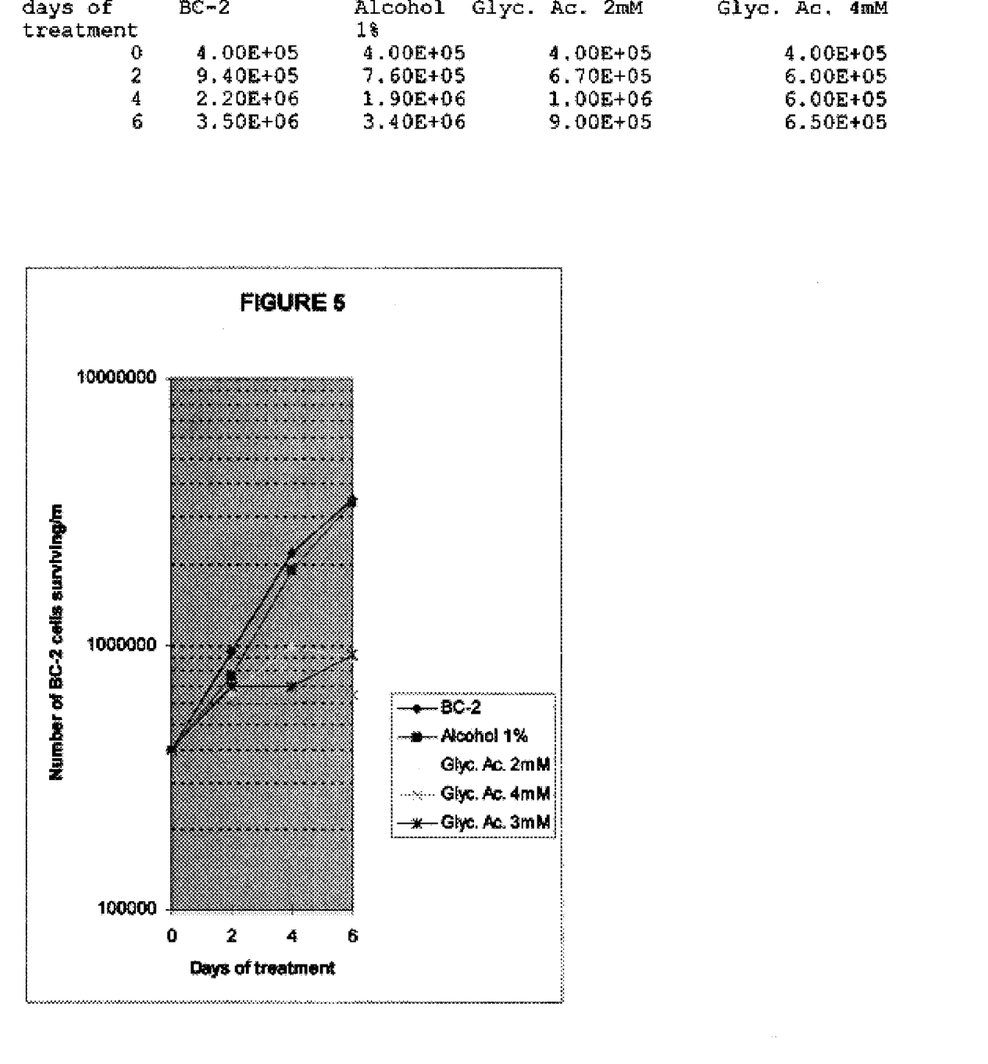
FIG. 5 demonstrates the effect of glycyrrhizic acid on BC-2 cells growth curve.
Figure 6:
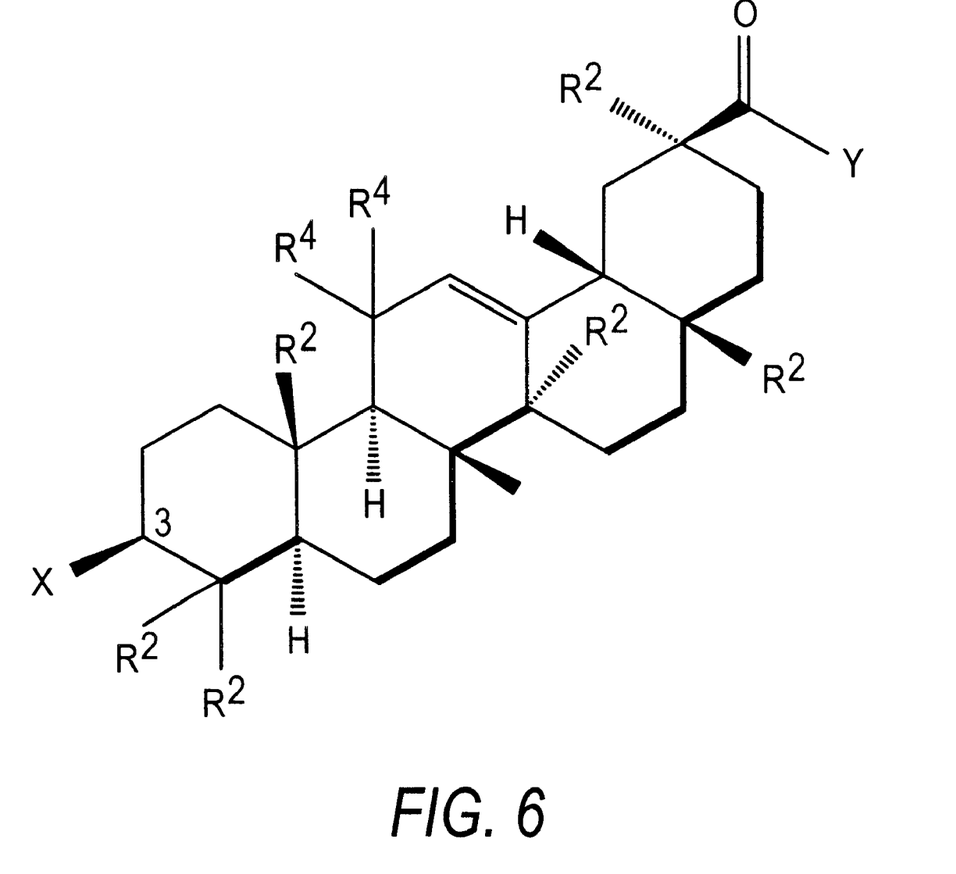
FIG. 6 shows the structural formula of the triterpenoid acid of the present invention.

FIGS. 4 and 5 demonstrate the effect of glycyrrhizic acid on BC-1 (FIG.4) and BC-2 (FIG. 5) cells growth curve. The cells are treated for six days with alcohol 1%, glycyrrhizic acid 2 mM (control), glycyrrhizic acid 3 mM and 4 mM in alcohol 0.5%, 0.75% and 1% respectively. After 6 days treatment cells growth decreased 50% using glycyrrhizic acid 2 mM and glycyrrhizic acid 3 mM. Cells growth decreased 80% using glycyrrhizic acid 4 mM. These results demonstrate that glycyrrhizic acid is inhibiting the proliferation of the EBV/KSHV infected cells and suggests that the drug has an activity against the Epstein Barr virus.

Immunofluorence Assay of BC-3 Cells
Immunofluorescence Assay (IFA)

To demonstrate the presence of latent KSHV antigens, cytospin preparations of KSHV-infected endothelial cells were fixed with methanol/acetone (1:1, vol/vol) solution at −20° C. for 15 min., and then stained as described by Kedes et al. with sera from three different KS patients, diluted 1:40 in master block (MB) containing PBS supplemented with 1% glycine, 2% BSA, 10% rabbit serum and 1% (wt/vol) HeLa cell sonicate. Secondary antibody FITC-conjugated F(ab')$_2$ fragment of rabbit antihuman IgG (DAKO, Carpinteria, Calif.) diluted 1:40 in MB was applied. Cell nuclei were counterstained for 5 min. in PBS containing 17 μM Dapi (4'-6'-diamino-2'-phenyidole dihydrochloride [Boehringer Mannheim Corp., Indianapolis, Ind.]), rinsed in TBST, mounted with Vectashield (Vector Lab. Inc., Burlingame, Calif.) and examined in a fluorescence microscope Axioplan2 (Zeiss, Germany). BC-3 cells were run in parallel as controls.

Figure 10:
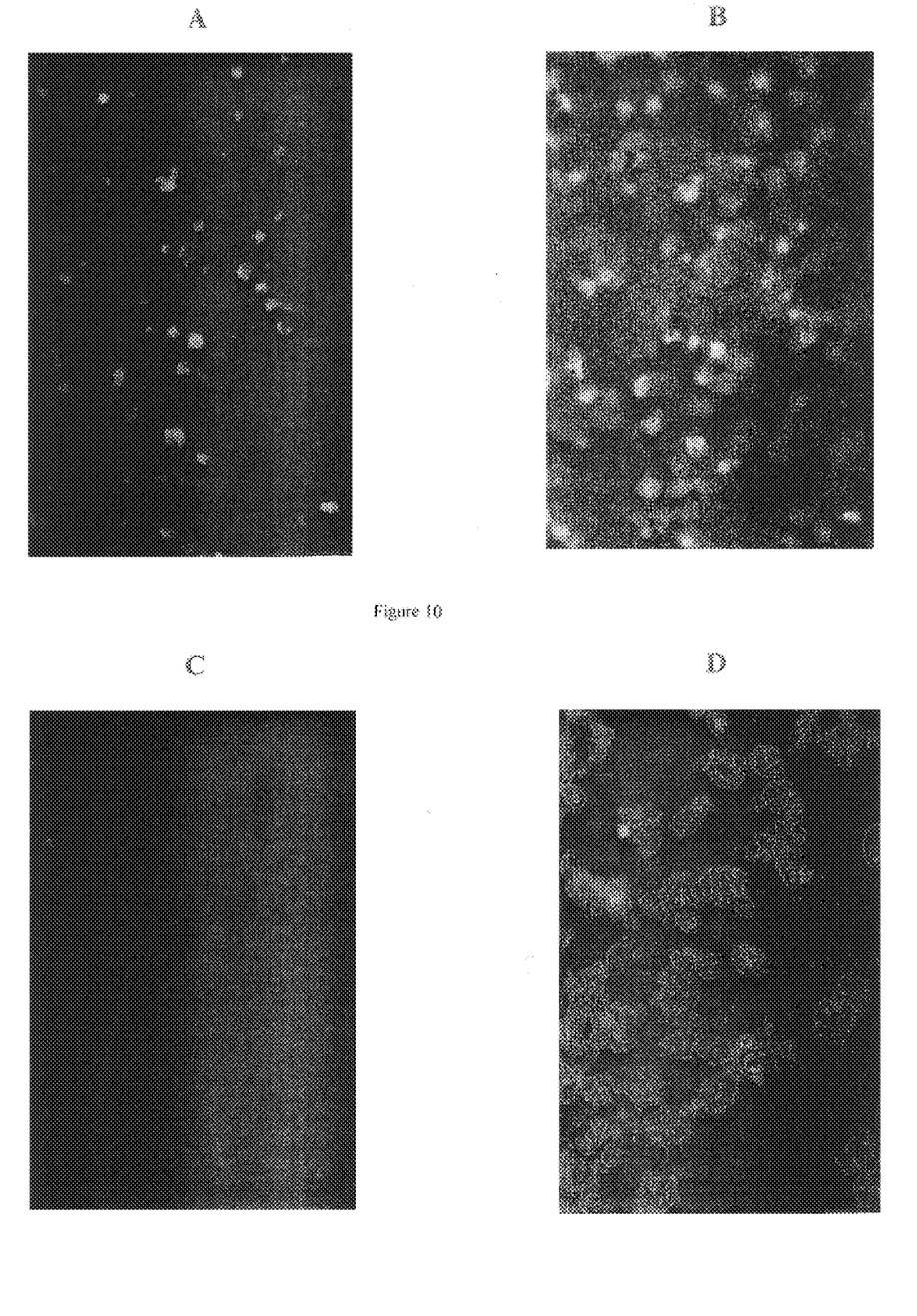
FIG. 10 shows an immunofluorence assay of BC-3 cells treated and untreated with a triterpenoid acid derivative of the present invention.

FIG. 10 shows an immunofluorence assay of BC-3 cells where panel A depicts BC-3 cells stained with KS patient serum. Panel B shows BC-3 cells stained with Dapi to localize the nuclei. In panel C the BC-3 cells have been treated with glycyrrhizic acid 4 mM and stained with KS patient serum. In panel D BC-3 cells have been treated with glycyrrhizic acid 4 mM and stained with Dapi to localize the nuclei. Kaposi's Sarcoma patient serum is used primary antibody to stain the KSHV latent antigens. The treatment with glycyrrhizic acid 4 mM inhibits the expression of latent viral antigens as demonstrated in panel C. As can be seen in this panel, speckled nuclear stainings typical of positive infected cells disappears after the treatment with glycyrrhizic acid.

I claim:

1. A method of treating Kaposi's sarcoma comprising the steps of administering to the patient a therapeutic amount of glycyrrhizic acid wherein the glycyrrhizic acid inhibits the transcription of viral latent genes of the Kaposi's sarcoma associated herpesvirus.

2. A method of treating Kaposi's sarcoma comprising the steps of administering to the patient a therapeutic a derivative of a triterpenoid acid containing a moiety of glycyrrhetinic acid wherein the moeity of glycyrrhetinic acid inhibits the transcription of viral latent genes.

3. The method according to claim 1 wherein the dosage for a child is about 10 mg to about 50 mg.

4. The method according to claim 2 wherein the dosage for a child is about 10 mg to about 50 mg.

5. The method according to claim 1 wherein the dosage for an adult is about 50 mg to about 1000 mg.

6. The method according to claim 2 wherein the dosage for an adult is about 50 mg to about 1000 mg.

7. The method according to claim 1 wherein the dosage is about 2.5 mg to about 50 mg/kg.

8. The method according to claim 2 wherein the dosage is about 2.5 mg to about 50 mg/kg.

9. The method according to claim 1 wherein the dosage is applied intranasally.

10. The method according to claim 2 wherein the dosage is applied intranasally.

11. The method according to claim 1 wherein the dosage is applied intravenously.

12. The method according to claim 2 wherein the dosage is applied intravenously.

13. The method according to claim 1 wherein the dosage is applied parenterally.

14. The method according to claim 2 wherein the dosage is applied parenterally.

15. A method of treating Kaposi's sarcoma according to claim 1 wherein the glycyrrhizic acid is in the form of a salt of glycyrrhizic acid.

16. A method of treating Kaposi's sarcoma according to claim 2 wherein the derivative of a triterpenoid acid containing a moeity of a salt of glycyrrhetinic acid.

17. A method of treating Kaposi's sarcoma comprising the steps of administering to the patient a therapeutic amount of glycyrrhizic acid wherein the glycyrrhizic acid inhibits the expression of latent viral antigens of the Kaposi's sarcoma associated herpesvirus.

18. A method of treating Kaposi's sarcoma comprising the steps of administering to the patient a therapeutic amount of a derivative of a triterpenoid acid containing a moiety of a salt of glycyrrhetinic acid wherein the salt of glycyyrrhetinic acid inhibits the expression of latent viral antigens of the Kaposi's sarcoma associated herpesvirus.

* * * * *